United States Patent [19]

Jung et al.

[11] Patent Number: 5,436,358
[45] Date of Patent: Jul. 25, 1995

[54] 2-(ARYL)PROPYLALKYLPOLYSILOXANE TYPE SILICONE FLUIDS AND METHODS OF MAKING THEM

[75] Inventors: Il N. Jung; Bok R. Yoo; Bong W. Lee, all of Seoul, Rep. of Korea

[73] Assignee: Korea Institute of Science and Technology, Seoul, Rep. of Korea

[21] Appl. No.: 302,189

[22] Filed: Sep. 8, 1994

[30] Foreign Application Priority Data

Dec. 1, 1993 [KR] Rep. of Korea ............... 1993-26071

[51] Int. Cl.$^6$ ............... C07F 7/10; C07F 7/08
[52] U.S. Cl. ............... 556/415; 556/456; 556/459; 556/429
[58] Field of Search ............... 556/456, 459, 415, 429

[56] References Cited

U.S. PATENT DOCUMENTS

| | | | |
|---|---|---|---|
| 3,088,964 | 5/1963 | Ryan | 556/456 |
| 4,873,011 | 10/1989 | Jung et al. | |
| 4,965,385 | 10/1990 | Jung et al. | |
| 5,075,477 | 12/1991 | Jung et al. | |
| 5,233,069 | 8/1993 | Jung et al. | |
| 5,235,061 | 8/1993 | Jung et al. | |
| 5,235,083 | 8/1993 | Jung et al. | |
| 5,300,669 | 4/1994 | Akamatsu | 556/456 |
| 5,302,734 | 4/1994 | Jung et al. | |
| 5,332,849 | 7/1994 | Jung et al. | |
| 5,338,876 | 8/1994 | Jung et al. | |

*Primary Examiner*—Paul F. Shaver
*Attorney, Agent, or Firm*—Oblon, Spivak, McClelland, Maier & Neustadt

[57] ABSTRACT

The present invention relates to novel cyclic or linear 2-(aryl)propylalkylpolysiloxane type silicone fluids as represented by the formula I and their preparation methods by hydrolyzing mixtures of 2-(aryl)propylalkyldichlorosilane and diorganodichlorosilane as represented by the formula II and formula III respectively.

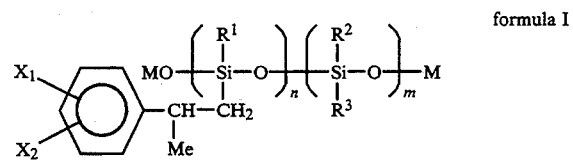

formula I

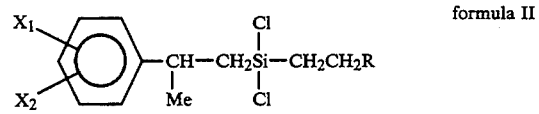

formula II

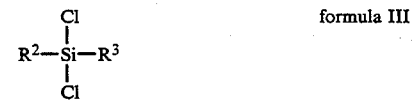

formula III wherein, $X_1$ and $X_2$ represent independently hydrogen or alkyl($C_1$-$C_3$), phenyl, phenoxy, fluoro, chloro, bromo, mercapto, mercaptomethyl group; $R^2$ and $R^3$ represent independently methyl or phenyl group; $R^1$ in the formula I is same as $CH_2CH_2R$ in formula II or cyclohexyl wherein R is $C_nH_{2n+2}$ (n=1-16), chloromethylene, cyanomethylene, phenyl, or cyano group; M represents H or $SiMe_3$ group wherein Me is methyl group and when M is hydrogen, the silanol groups at the both ends of the molecule easily undergo dehydration and cyclize to form the cyclic silicone fluids; n and m can be 2-200 and the ratio n/m can be 1:0.01-1:100.

15 Claims, No Drawings

2-(ARYL)PROPYLALKYLPOLYSILOXANE TYPE SILICONE FLUIDS AND METHODS OF MAKING THEM

BACKGROUND OF THE INVENTION

1. Field of the Invention

The present invention relates to novel cyclic or linear 2-(aryl)propylalkylpolysiloxane type silicone fluids as represented by the formula I and their preparation methods by hydrolyzing mixtures of 2-(aryl)propylalkyldichlorosilane and diorganodichlorosilane as represented by the formula II and formula III respectively.

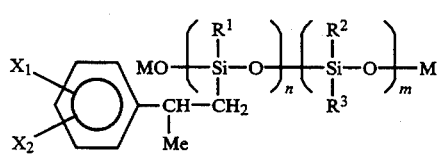

formula I

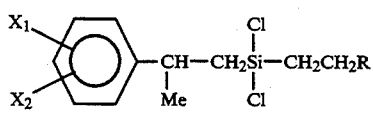

formula II

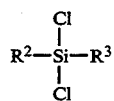

formula III wherein, $X_1$ and $X_2$ represent independently hydrogen or alkyl($C_1$-$C_3$), phenyl, phenoxy, fluoro, chloro, bromo, mercapto, mercaptomethyl group; $R^2$ and $R^3$ represent independently methyl or phenyl group; $R^1$ in the formula I is same as $CH_2CH_2R$ in formula II or cyclohexyl wherein R is $C_nH_{2n+2}$ (n=1-16), chloromethylene, cyanomethylene, phenyl, or cyano group; M represents H or $SiMe_3$ group wherein Me is methyl group and when M is hydrogen, the silanol groups at the both ends of the molecule easily undergo dehydration and cyclize to form the cyclic silicone fluids; n and m can be 2-200 and the ratio n/m can be 1:0.01-1:100.

2. Description of the Prior Art

It is well known in the art that polymethylhydrogensiloxanes when applied to textile fabrics, are capable of imparting softening and water repellency thereto. (Walter Noll, Chemistry and Technology of Silicone, Academic Press, 1968, p-196)

In general, the preparation of organosilicone fluids is performed by the hydrolysis and condensation of organosilanes, such as those having two methyl or other organic radicals bonded to the silicon atoms, has theretofore been described. The hydrolysis is conducted by reacting a chlorosilane, such as dimethyldichlorosilane, with water, generally in the presence of an inert solvent. The organosilicone fluids are thus obtained without difficulty. (Wilcock, U.S. Pat. No. 2,491,843, Patnode and Wilcock, J. Am. Chem. Soc., 68, 358 (1946)) Dimethyldichlorosilane gives with water a mixture of polydimethylcyclosiloxanes and linear polydimethylsiloxane-a,ω-diols. Depending upon the hydrolysis methods, the ratio of cyclic and linear fluids in the products varies. Hydrolysis with dilute hydrochoric acid or the employment of organic solvent in hydrolysis can increase the proportion of cyclic fluids. The so-called "reversed" hydrolysis, in which a calculated amount of water is added to the mixture of organochlorosilanes, is recommended for the "reversed" hydrolysis has been recommended for the co-hydrolysis of silane mixtures of dichlorodimethylsilane and methyltrichlorosilane, methyltrichlorosilane and chlorotrimethylsilane, or of diorganidichlorosilanes with different organic substituents. (walter Noll, Chemistry and Technology of Silicone, Academic Press, 1968, p-196) The special modified silicone fluids can be prepared by replacing a proportion of the methyl groups in polydimethylsiloxanes by other organic groups such as phenyl, vinyl, hydrido, etc. The chlorosilanes may be dissolved in an inert organic solvent such as toluene, benzene, carbon tetrachloride, ether, liquid aliphatic hydrocarbons.

The present inventors reported that allyldichlorosilane as the major product and allyltrichlorosilane were prepared by reacting allyl chloride, incorporated with hydrogen chloride with elemental silicon in the presence of copper catalyst at a temperature from 250° C. to 350° C. Cadmium was a good promoter and the reaction could be carried out in a fluidized bed or a stirred bed reactor. The incorporation of hydrogen chloride suppressed the decomposition of allylchloride and prevented the production of diallyldichlosilane. Diallyldichlosilane easily caused the polymerization of the products at the reaction temperature. [Korean Patent Application No. 92-10292 ('92.6.13)]

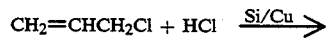

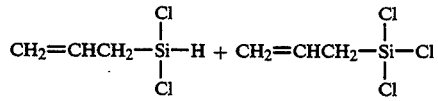

The present inventors also reported the preparation of 2-(aryl)propyldichlorosilane by the Friedel-Craft reaction of allyldichlorosilane with aromatic compounds using aluminum chloride as a catalyst. Aromatic compounds could be benzene, alkyl substituted benzenes, halogen substituted benzenes, thiol or mercaptoalkyl substituted benzenes, naphthalene, biphenyl, biphenyl ethers, etc. [Korean Patent Application No. 92-12996 ('92.7.21)]

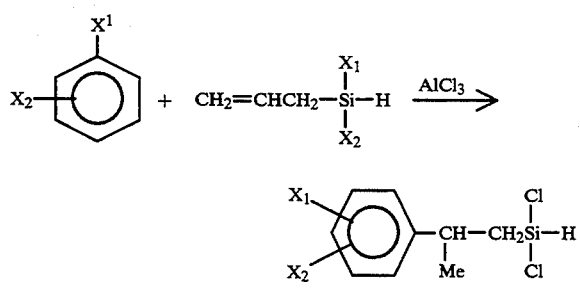

The present inventors also reported the preparation of 2-(aryl)propylalkyldichlorosilane as represented by the formula II by the hydrosilation reaction of 2-(aryl)propyldichlorosilane prepared as above with a various olefins in the presence of platinum catalyst. [Korean Patent Application No. 92-22996 ('92.12.1)]

SUMMARY OF THE INVENTION

The present invention relates to novel cyclic or linear 2-(aryl)propylalkylpolysiloxane type silicone fluids as represented by the formula I and their preparation methods by hydrolyzing mixtures of 2-(aryl)propylalkyldichlorosilane and diorganodichlorosilane as represented in formula II and formula III respectively.

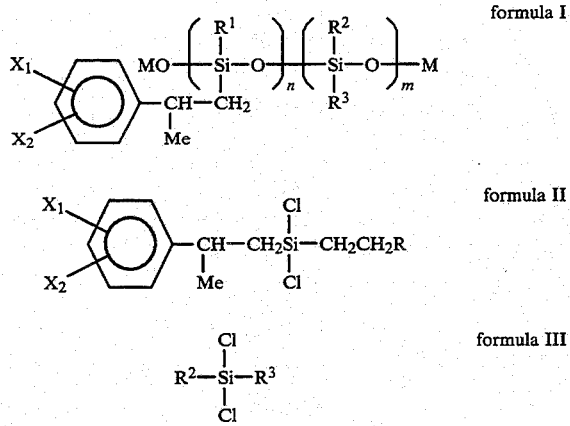

formula I formula II formula III wherein, $X_1$ and $X_2$ represent independently hydrogen or alkyl($C_1$-$C_3$), phenyl, phenoxy, fluoro, chloro, bromo, mercapto, mercaptomethyl group; $R^2$ and $R^3$ represent independently methyl or phenyl group; $R^1$ in the formula I is same as $CH_2CH_2R$ in formula II or cyclohexyl wherein R is $C_nH_{2n+2}$ (n=1-16), chloromethylene, cyanomethylene, phenyl, or cyano group; M represents H or $SiMe_3$ group wherein Me is methyl group and when M is hydrogen, the silanol groups at the both ends of the molecule easily undergo dehydration and cyclize to form the cyclic silicone fluids; n and m can be 2-200 and the ratio n/m can be 1:0.01-1:100.

DETAILED DESCRIPTION OF THE INVENTION 2-(aryl)propylalkylpolysiloxanes type silicone fluids as represented by the formula I may be prepared by any suitable methods. For example, 2-(aryl)propylalkylpolysiloxanes end-blocked with hydroxy group or trimethylsiloxy groups are prepared by hydrolyzing 2-(aryl)propylalkyldichlorosilane or a mixture of trimethylchlorosilane and 2-(aryl)propylalkyldichlorosilane. The chlorosilanes may be dissolved in an inert organic solvent such as toluene, benzene, carbon tetrachloride, ether, liquid aliphatic hydrocarbons, etc. and then hydrolyzed by pouring the solution into water or the other way around. After hydrolysis the solution has been thoroughly washed with water to remove all, or substantially all, of the hydrochloroic acid and then the solvent may be distilled to give the fluids. 2-(Aryl)propylalkylpolysiloxanes end-blocked with hydroxy group are prepared by hydrolyzing 2-(aryl)propylalkyldichlorosilane only. The same fluids end-blocked with trimethylsiloxy groups may be prepared by co-hydrolyzing 2-(aryl)propylalkyldichlorosilane (III) and trimethylchlorosilane or equilibrizing 2-(aryl)propylalkylpolysiloxanes end-blocked with the hydroxy group and hexamethyldisiloxane using concentrated sulfuric acid or $CF_3SO_3H$. The copolymers containing diorganosiloxy- and 2-(aryl)propylalkylsiloxy-groups may be prepared by co-hydrolyzing diorganodichlorosilane and 2-(aryl)propylalkyldichlorosilane and then equilibrating the products with hexamethyldisiloxane. The same fluids may be prepared by equilibrating 2-(aryl)propylalkylpolysiloxanes end-blocked with trimethylsloxy group and cyclic diorganopolysiloxanes using concentrated sulfuric acid or $CF_3SO_3H$.

The invention will be further illustrated by the following examples. It is, however, not intended that this invention will be limited by the examples.

EXAMPLE 1

To a 300 ml, three neck, round bottomed flask equipped with a mechanical stirrer, a dropping funnel, and a condenser were added 5 g (0.017 mol) of 6-phenyl-1,4,4-trichloro-4-silaheptane and 30 ml of ether. Through the dropping funnel was added dropwise 20 ml of water over 30 min. After the solution was reacted for another hour with stirring, the organic layer was separated and washed three times with 20 ml of distilled water. The solution was dried over $Mg_2SO_4$ and distilled under reduced pressure to remove the solvent. This product was very viscose liquid. The amount of the obtained product was 4.0 g. The GPC analysis result of this product represented by means molecular weight of 500-3,000.

EXAMPLE 2

The same procedure as Example 1 was repeated except that 9-phenyl-7,7-dichloro-7-siladecane (6.1 g, 0.02 mol) was used instead of 6-phenyl-1,4,4-trichloro-1-silaheptane. The amount of the obtained product was 4.9 g. The GPC analysis result of this product represented by mean molecular weight of 500-3,000.

EXAMPLE 3

The same procedure as Example 1 was repeated except that a mixture of 5-phenyl-3,3-dichloro-1-cyclohexyl-3-silahexane (4.5 g, 0.015 mol) was used instead of 6-phenyl-1,4,4-trichloro-1-silaheptane. The amount of the obtained product was 3.5 g. The GPC analysis result of this product represented by mean molecular weight of 500-3,000.

EXAMPLE 4

The same procedure as Example 1 was repeated except that a mixture of 5-(3 & 4-methylphenyl)-3,3-dichloro-1-phenyl-3-silahexane (7.0 g, 0.02 mol) was used instead of 6-phenyl-1,4,4-trichloro-4-silaheptane. The amount of the obtained product was 5.8 g. The GPC analysis result of this product represented by mean molecular weight of 500-3,000.

NMR data of this type polymers prepared by hydrolyzing various organochlorosilanes according to the procedures described above are listed in Table 1.

TABLE 1

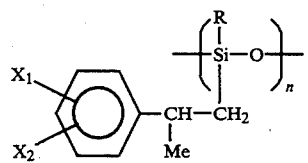

| X₁ | X₂ | R | SiCH₂ | CH₃ | CH | Aryl-H | X₁ and X₂/R |
|---|---|---|---|---|---|---|---|
| H | H | (CH₂)₃Cl | 0.94–1.14 | 1.32–1.36 | 2.94–3.06 | 7.16–7.32 | 0.45–0.61, 1.64–1.78 and 3.40–3.53(m, 2H, CH₂) |
| H | H | (CH₂)₅CH₃ | 0.89–1.11 | 1.28–1.45 | 3.22–3.30 | 6.89–7.19 | 0.43–0.61(br.s, 2H, CH₂), 0.95–1.12(br.t, 3H, CH₃), 1.28–1.45(br.s, 8H, CH₂) |
| H | H | (CH₂)₁₇CH₃ | 0.89–1.11 | 1.28–1.41 | 3.20–3.31 | 6.89–7.21 | 0.43–0.61(br.s, 2H, CH₂), 0.95–1.12(br.t, 3H, CH₃), 1.28–1.45(br.s, 30H, CH₂) |
| H | H | (CH₂)₂Ph | 0.93–1.15 | 1.29–1.43 | 3.21–3.34 | 6.91–7.33 | 2.33(s, 3H, CH₃)/0.44–0.64(br.m, 2H, CH₂), 2.58–2.70(br.m, 2H, CH₂), 6.91–7.33(m, 5H, phenyl-H) |
| H | H | Cyclohexyl | 0.89–1.12 | 1.30–1.47 | 3.23–3.37 | 6.93–7.48 | 0.50–0.73(br.m, 1H, CH), 1.09–1.33(br.m, 4H, CH₂), 1.62–1.85(br.m, 6H, CH₂) |
| H | H | (CH₂)₂CN | 0.90–1.11 | 1.31–1.36 | 2.93–3.07 | 7.12–7.32 | 0.52–0.67(br.s, 2H, CH₂), 2.46 br.t, 2H, CH₂) |
| H | m & p-Me | (CH₂)₅CH₃ | 0.89–1.10 | 1.29–1.45 | 3.21–3.31 | 6.90–7.20 | 2.35(br.s, 3H, CH₃)/0.43–0.61(br.s, 2H, CH₂), 0.95–1.12(br.t, 3H, CH₃), 1.28–1.45(br.s, 8H, CH₂) |
| H | m & p-Me | (CH₂)₂Ph | 0.92–1.15 | 1.27–1.44 | 3.19–3.33 | 6.93–7.32 | 2.35(br.s, 3H, CH₃)/0.45–0.63(br.m, 2H, CH₂), 2.58–2.70(br.m, 2H, CH₂), 7.91–7.34(m, 5H, phenyl-H) |
| H | m & p-Me | Cyclohexyl | 0.92–1.12 | 1.31–1.47 | 3.24–3.37 | 6.95–7.48 | 2.33(s, 3H, CH₃)/0.50–0.73(br.m, 1H, CH), 1.09–1.33(br.m, 4H, CH₂), 1.61–1.83(br.m, 6H, CH₂) |
| H | m & p-Et | (CH₂)₃Cl | 0.93–1.13 | 1.30–1.42 | 2.89–3.03 | 7.02–7.27 | 0.45–0.60, 1.65–1.80 and 3.37–3.48(br.m, 2H, CH₂)/ 1.22–1.28(br.s, 3H, CH₃), 2.59–2.69(br.s, 2H, CH₂) |
| H | m & p-iso-pr | (CH₂)₃Cl | 1.00–1.18 | 1.28–1.40 | 2.85–3.05 | 6.91–7.29 | 0.42–0.61, 1.60–1.79 and 3.32–3.43(br.m, 2H, CH₂)/ 1.21–1.29(br.m, 6H, CH₃), 2.85–3.05(br.m, 1H, CH) |
| H | o-F | (CH₂)₃Cl | 0.90–1.12 | 1.25–1.38 | 3.29–3.45 | 6.92–7.27 | 0.43–0.63, 1.63–1.80 and 3.38–3.48(br.m, 2H, CH₂) |
| H | p-F | (CH₂)₃Cl | 0.90–1.12 | 1.25–1.38 | 2.83–3.05 | 6.92–7.27 | 0.43–0.63, 1.63–1.80 and 3.38–3.48(br.m, 2H, CH₂) |
| H | o-Cl | (CH₂)₃Cl | 0.85–1.12 | 1.23–1.39 | 3.39–3.58 | 7.10–7.37 | 0.45–0.82, 1.65–1.85 and 3.39–3.58(br.m, 2H, CH₂) |
| H | p-Cl | (CH₂)₃Cl | 0.85–1.12 | 1.23–1.39 | 2.87–3.00 | 7.10–7.37 | 0.45–0.82, 1.65–1.85 and 3.39–3.58(br.m, 2H, CH₂) |
| H | o-Br | (CH₂)₃Cl | 0.86–1.13 | 1.20–1.38 | 3.37–3.52 | 7.00–7.54 | 0.45–0.81, 1.61–1.82 and 3.38–3.56(br.m, 2H, CH₂) |
| H | p-Br | (CH₂)₃Cl | 0.86–1.13 | 1.20–1.38 | 2.85–2.98 | 7.00–7.54 | 0.45–0.81, 1.64–1.82 and 3.38–3.56(br.m, 2H, CH₂) |
| H | m & p-Ph | (CH₂)₃Cl | 0.99–1.20 | 1.30–1.41 | 3.00–3.14 | 7.25–7.65 | 7.25–7.65(m, 5H, Phenyl-H)/0.48–0.66, 1.65–1.85 and 3.36–3.49(br.m, 2H, CH₂) |
| H | m & p-OPh | (CH₂)₅CH₃ | 0.91–1.12 | 1.32–1.47 | 3.23–3.34 | 6.95–7.15 | 0.43–0.60(br.s, 2H, CH₂), 0.94–1.10(br.t, 3H, CH₃), 1.30–1.47(br.s, 8H, CH₂) |
| H | m & p-SH | (CH₂)₅CH₃ | 0.91–1.12 | 1.31–1.46 | 3.22–3.32 | 6.99–7.39 | 2.81–3.02(br.s, 1H, SH)/0.44–0.61(br.s, 2H, CH₂), 0.95–1.11(br.t, 3H, CH₃), 1.31–1.49(br.s, 8H, CH₂) |
| H | m & p-CH₂SH | (CH₂)₅CH₃ | 0.91–1.12 | 1.31–1.46 | 3.22–3.32 | 709–7.43 | 3.25–3.37(s, 2H, CH₂), 2.85–3.05(s, 1H, SH)/0.44–0.61 (s, 2H, CH₂), 0.95–1.11(t, 3H, CH₃), 1.31–1.49(s, 8H, CH₂) |
| 2 & 3-Me | 3 & 4-Me | (CH₂)₃Cl | 0.89–1.11 | 1.20–1.43 | 2.85–3.05 | 6.87–7.12 | 2.30(br.s, 6H, CH₃)/1.17–1.43(CH₂), |
| 2 & 3-Me | 3 & 4-Me | (CH₂)₂Ph | 0.91–1.14 | 1.26–1.45 | 3.18–3.33 | 6.92–7.34 | 2.35(br.s, 6H, CH₃)/0.44–0.63(br.m, 2H, CH₂), 2.58–2.70(br.m, 2H, CH₂), 7.92–7.34(m, 5H, phenyl-H) |
| 2-Me | 5-Me | (CH₂)₅CH₃ | 0.91–1.10 | 1.31–1.48 | 3.24–3.33 | 6.95–7.15 | 2.38(Br.s, 6H, CH₃)/0.43–0.61(br.s, 2H, CH₂), 0.95–1.11(br.t, 3H, CH₃), 1.31–1.48(br.s, 8H, CH₂) |
| 2-Me | 5-Me | Cyclohexyl | 0.93–1.13 | 1.30–1.47 | 3.23–3.38 | 6.94–7.49 | 2.34(s, 6H, CH₃)/0.50–0.73(br.m, 1H, CH), 1.09–1.33(br.m, 4H, CH₂), 1.61–1.83(br.m, 6H, CH₂) |
| 2-Me | 5-Me | (CH₂)₃CN | 0.91–1.11 | 1.30–1.40 | 3.00–3.10 | 6.09–7.30 | 0.51–0.65 and 1.22–1.40(br.s, 2H, CH₂), 2.48(br.t, 2H, CH₂) |

EXAMPLE 5

Using the same apparatus described in Example 1, 20 ml of ethyl ether and 20 ml of water were placed in the flask. To the flask a mixture of 6-(3,4-dimethylphenyl)-1,4,4-trichloro-4-silaheptane (4.1 g, 0.013 mol) and dimethyldichlorosilane (1.3 g, 0.01 mol) was added dropwise through the additional funnel over 30 min. After the solution was reacted for another hour with stirring, the organic layer was separated and washed three times with 20 ml of distilled water. The solution was dried over Mg₂SO₄ and distilled under reduced pressure to remove the solvent. The amount of the obtained product was 3.8 g, after devolatilization at 80° C. under vacuum. The GPC analysis result of this product represented by mean molecular weight of 500–20,000.

NMR data of this type co-polymeric products were similar to those of the corresponding co-polymer of Table 1 except the broad peak at 0.05–0.22 ppm due to dimethylsiloxy group.

EXAMPLE 6

The same procedure as Example 5 was repeated except that a mixture of 5-(2- or 4-fluorophenyl)-1,4,4-trichloro-4-silaheptane (6.27 g, 0.012 mol) and dimethyldichlorosilane (0.03 g, 0.0002 mol) was used. The amount of the obtained product was 5.9 g with the molecular weight of 500–5,000.

Other compounds represented by the formula II besides 5-(2- or 4-fluorophenyl)-1,4,4-trichloro-4-silaheptane can be co-hydrolyzed with dimethyldichlorosilane as above and similar type of co-polymers obtained.

EXAMPLE 7

The same procedure as Example 5 was repeated except that a mixture of 6-(3- or 4-mercaptophenyl)-1,4,4-trichloro4-silaheptane (0.16 g, 0.0005 mol) and dimethyldichlorosilane (6.5 g, 0.05 mol) was used. The amount of the obtained product was 3.0 g with the molecular weight of 200–40,000.

Other compounds represented by the formula II besides 6-(3- or 4-mercaptophenyl)-1,4,4-trichloro-4-silaheptane can be co-hydrolyzed with dimethyldichlorosilane as above and similar type of co-polymers obtained.

EXAMPLE 8

The same procedure as Example 5 was repeated except that a mixture of 6-(4-chlorophenyl)-1,4,4-trichloro-4-silaheptane (4.0 g, 0.012 mol) and dimethyldichlorosilane (1.52 g, 0.011 mol) was used. The amount of the obtained product was 3.9 g with the molecular weight of 500–20,000.

Other compounds represented by the formula II besides 6-(4-chlorophenyl)-1,4,4-trichloro-1-silaheptane can be co-hydrolyzed with methylphenyldichlorosilane as above and similar type of co-polymers obtained. NMR data of this type co-polymeric products were similar to those of the corresponding co-polymer of Table 1 except the broad peak at 0.09–0.40 ppm due to methyl group on silicon. The peaks due to phenylsiloxy group overlap with the peaks due to phenyl group of 6-(4-chlorophenyl)-1,4,4-trichloro-4-silaheptane. The other peaks were similar to those in Table 1.

EXAMPLE 9

The same procedure as Example 5 was repeated except that a mixture of 6-(3- & 4-phenoxyphenyl)-1,4,4-trichloro4-silaheptane (4.3 g, 0.011 mol), dimethyldichlorosilane (1.3 g, 0.011 mol), and trimethylchlorosilane 0.2 g (0.002 mol) was used. The amount of the obtained product was 2.3 g with the molecular weight of 500–5,000.

Other compounds represented by the formula II besides 6-(4-chlorophenyl)-1,4,4-trichloro-4-silaheptane can be co-hydrolyzed with methylphenyldichlorosilane as above and similar type of co-polymers obtained. NMR data of this type co-polymeric products were similar to those of the corresponding co-polymer of Table 1 except the broad peak at 0.01–0.23 ppm due to trimethylsilyl group.

What is claimed is:

1. A 2-(aryl)propylalkylpolysiloxane silicone fluid having formula I

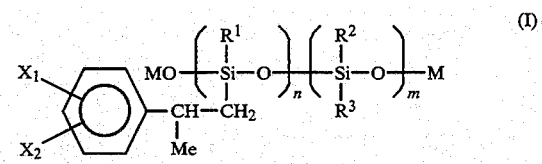

wherein $X_1$ or $X_2$, independently, is phenyl, phenoxy, fluoro, chloro, bromo, mercapto or mercaptomethyl; $R^1$ is cyclohexyl or $CH_2CH_2R$ where R is $C_nH_{2n+2}$ and $n=1-16$, chloromethylene, cyanomethylene, phenyl or cyano; M is H or $SiMe_3$ and Me is a methyl group, $R^2$ and $R^3$ independently, are methyl or phenyl; the sum of n and m is 2–200; and the ratio of n/m is 1:0–1:100.

2. The fluid of claim 1, wherein $X_1$ or $X_2$ is phenyl.
3. The fluid of claim 1, wherein $X_1$ or $X_2$ is phenoxy.
4. The fluid of claim 1, wherein $X_1$ or $X_2$ is chloro, fluoro or bromo.
5. The fluid of claim 1, wherein $X_1$ or $X_2$ is mercapto.
6. The fluid of claim 1, wherein $X_1$ or $X_2$ is mercaptomethyl.
7. The fluid of claim 1, wherein R is said $CH_2CH_2R$.
8. The fluid of claim 1, wherein m is 0.
9. The fluid of claim 1, wherein said ratio is 0:0.1–1:100.
10. A 2-(aryl)propylalkylpolysiloxane silicone fluid having formula I

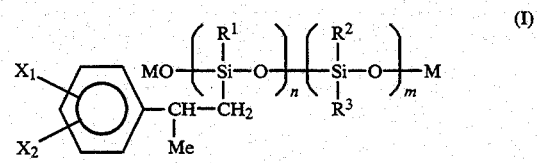

wherein $X_1$ and $X_2$, independently, are hydrogen, $C_1$–$C_3$-alkyl, phenyl, phenoxy, fluoro, chloro, bromo, mercapto or mercaptomethyl; $R^1$ is chloromethylene, cyanomethylene or cyano; M is H or $SiMe_3$ and Me is a methyl group; $R^2$ and $R^3$, independently, are methyl or phenyl; the sum of n and m is 2–200; and the ratio of n/m is 1:0–1:100.

11. The fluid of claim 10, wherein $R^1$ is chloromethylene.
12. The fluid of claim 10, wherein $R^1$ is cyanomethylene.
13. The fluid of claim 10, wherein $R^1$ is cyano.
14. The fluid of claim 10, wherein said ratio is 1:0.01–1:100.
15. The fluid of claim 10, wherein m=0.

* * * * *